US00PP25130P3

(12) United States Plant Patent
Bjorge et al.

(10) Patent No.: US PP25,130 P3
(45) Date of Patent: Dec. 2, 2014

(54) PEACH TREE NAMED 'FA 1566'

(50) Latin Name: *Prunus persica*
Varietal Denomination: FA 1566

(71) Applicants: Annette Bjorge, Coloma, MI (US); Randy Bjorge, Coloma, MI (US)

(72) Inventors: Annette Bjorge, Coloma, MI (US); Randy Bjorge, Coloma, MI (US)

( * ) Notice: Subject to any disclaimer, the term of this patent is extended or adjusted under 35 U.S.C. 154(b) by 18 days.

(21) Appl. No.: 13/986,172

(22) Filed: Apr. 9, 2013

(65) Prior Publication Data

US 2014/0304864 P1 Oct. 9, 2014

(51) Int. Cl.
*A01H 5/00* (2006.01)

(52) U.S. Cl.
USPC ..... Plt./198

(58) Field of Classification Search
CPC ..... A01H 5/00
USPC ..... Plt./198, 194
See application file for complete search history.

*Primary Examiner* — June Hwu
*Assistant Examiner* — Keith Robinson

(57) ABSTRACT

A new and distinct variety of peach tree 'FA 1566' originating as the result of a cross between 'Fayette' (an unpatented selection) and 'Newhaven' (an unpatented selection). The new variety is unique in that it is 80% to 90% red with a background of orange-red with dark red highlights and ripens early.

2 Drawing Sheets

Latin name of the genus and species of the plant claimed: *Prunus persica.*

Variety denomination: 'FA 1566'.

FIELD OF THE INVENTION

The new variety, 'FA 1566' was developed in a breeding program as a cross between 'Fayette' (an unpatented selection) and 'Newhaven' (an unpatented selection). The parent tree was grown and evaluated in Coloma, Mich.

BACKGROUND OF THE INVENTION

A new and distinct variety of peach tree originating in 1990 as a result of a cross between 'Fayette' (an unpatented selection) and 'Newhaven' (an unpatented selection). The new variety is unique from 'Fayette' in that it is 80% to 90% red with a background of orange-red with dark red highlights and ripens 9 days earlier and is unique from Newhaven in that it is 80% to 90% red with a background of orange-red with dark red highlights and ripens 18 days later.

SUMMARY OF THE INVENTION

This new and distinct variety of FA 1566 tree was bred in 1990, was developed in a peach breeding program in Coloma Mich. as a cross between Fayette (an unpatented selection) and Newhaven (an unpatented selection). Observations during the next two seasons confirmed that the fruit colored to an 80 to 90% orange/red color and ripens two to three days before Cresthaven (an unpatented selection).

In August of 2000, buds were taken from the original tree and trees for further testing were asexually produced by chip budding onto Lovell (an unpatented selection) rootstock in Ephrata, Wash. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained at Coloma, Mich.

DETAILED BOTANICAL DESCRIPTION

Figure 1:
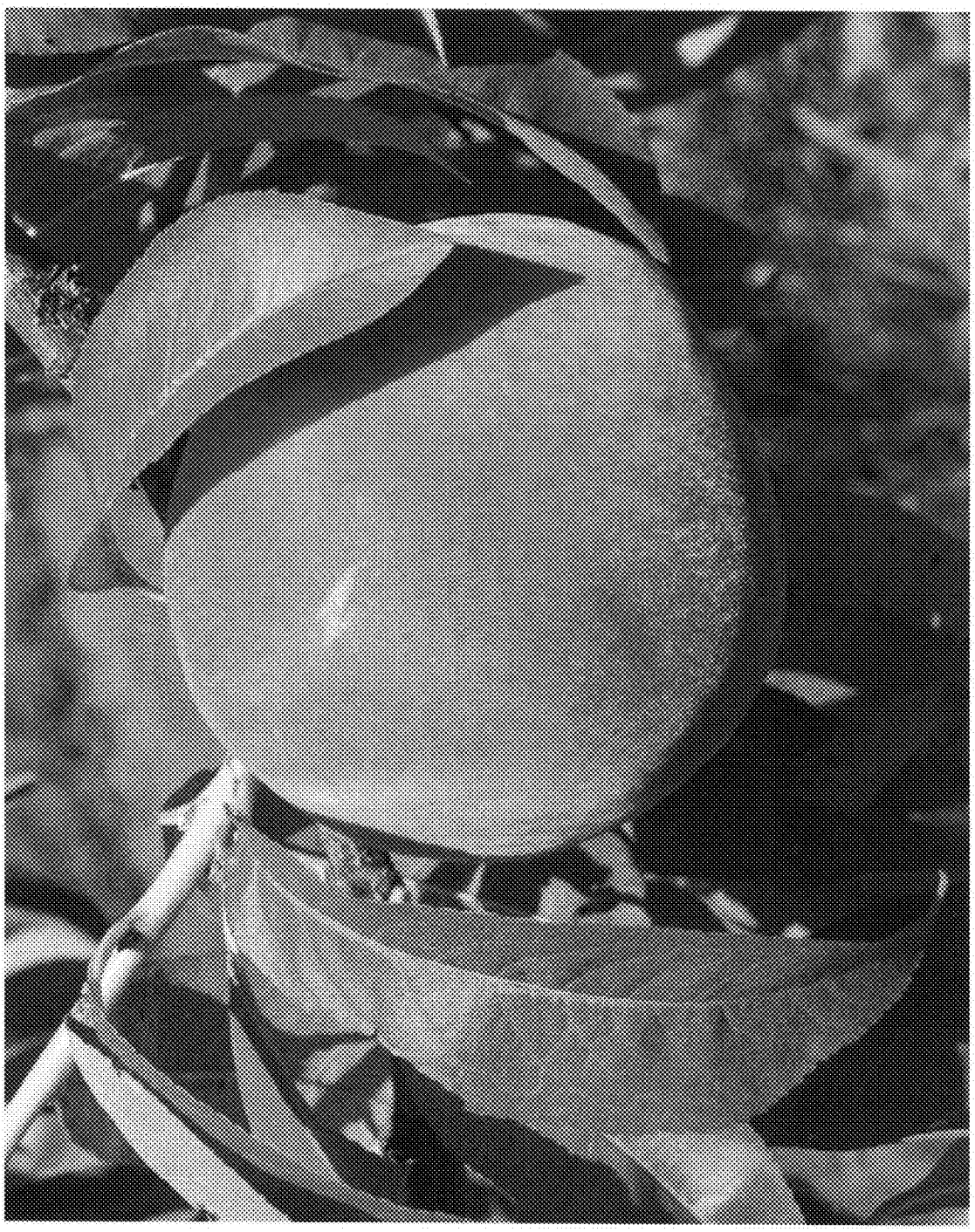
FIG. 1 illustrates the fruit and foliage of the new variety at maturity.
Figure 2:
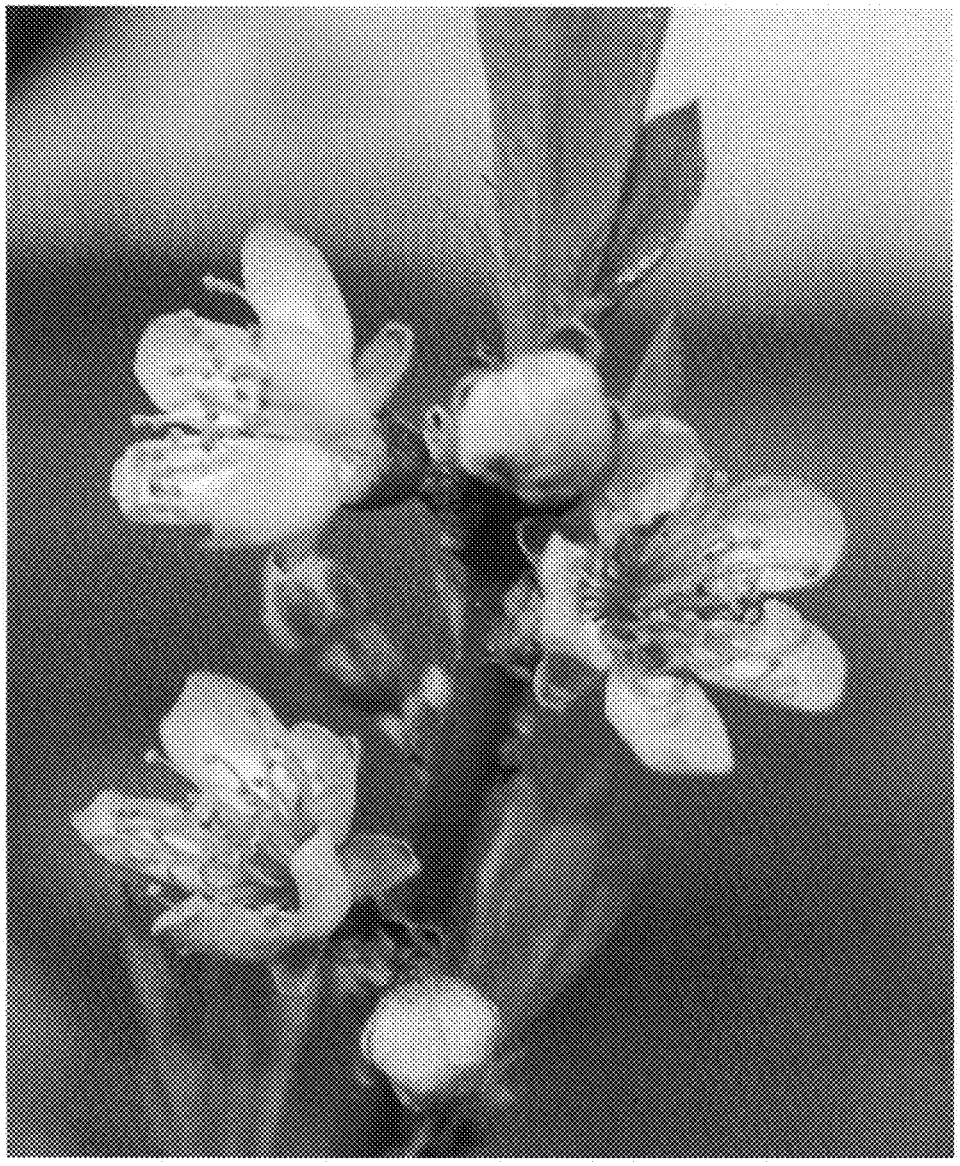
FIG. 2 illustrates blossoms and buds of the new variety.

A detailed description of the 'FA 1566' cultivar follows using The Royal Horticultural Society of London Colour Chart, 1986 edition, for color identification except where general color terms are sufficient.

Parentage: Fayette×Newhaven. Locality of the original discovery and observations is Coloma, Mich.

Tree:
- *Age.*—10 years.
- *Size.*—Height 2.5 m, width 3.5 m.
- *Vigor.*—Vigorous, yearly growth averages 1 m.
- *Density.*—Medium thick.
- *Form.*—Upright-spreading.
- *Production.*—Productive, averaging 400 bushels per acre.
- *Growth type.*—Non-spur.
- *Bearing.*—Annual.

Trunk:
- *Size.*—16 cm in diameter at 100 cm above ground level.
- *Surface.*—Very rough, flaking.
- *Bark color.*—Grey 201A.
- *Lenticels.*—Length 20 cm, width 3 cm.
- *Lenticel color.*—Grayed Orange 165B.

Branches:
- 3 *year old branch.*—Diameter 30 mm, color. Grayed Orange 166C, angle to trunk 90°, texture rough.
- 2 *year old branch.*—Diameter 10 mm, length 25 cm, color Grayed Orange 165B, texture rough.
- 1 *year old branch.*—Diameter 8 mm, length 30 cm, color Grayed Purple 183A on upper surfaces, Yellow Green 146C on lower surfaces, texture smooth.

Leaves:

*Leaf bud density.*—Medium dense, average internode spacing of 12 mm to 15 mm.

*Thickness.*—Medium thin, 0.05 mm or less.

*Size.*—Length 170 mm, width 40 mm.

*Texture.*—Leathery, crisp.

*Form.*—Long, lanceolate.

*Base.*—Cuneate.

*Apex.*—Narrowly acuminate with slight curve at tip.

*Upper surface color.*—Yellow Green 146A.

*Lower surface color.*—Yellow Green 146B.

*Venation.*—Alternate, 18 veins, color Yellow Green 146.

*Mid-vein.*—Upper surface color Yellow Green 152A, lower surface color Yellow Green 153A.

*Margin.*—Dentate, ruffled.

*Petiole length.*—12 mm.

*Petiole width.*—9 mm.

*Petiole upper surface color.*—Yellow Green 152A.

*Petiole lower surface color.*—Yellow Green 153A.

*Petiole groove.*—Width 1.5 mm, depth 1 mm.

*Stipules.*—None observed.

*Leaf glands.*—Reniform, 3 to 4 at base of leaf on petiole, length 0.3 mm, width 0.3 mm.

*Leaf gland color.*—Grayed Orange 165B.

Leaf buds:

*Length.*—5 mm.

*Width.*—1 mm.

*Color.*—Grayed Green 189A.

*Internode distance.*—12 mm to 15 mm.

*Placement.*—Tightly applied to branch.

Flowers:

*Bloom period.*—Mid-season, April 25 to May 5 in Coloma, Mich.

*Duration of bloom.*—5 to 7 days dependent on weather conditions.

*Presentation.*—Semi-showy.

*Fragrance.*—Light.

*Fertility.*—Self-fertile.

*Pollen.*—Present.

Flowers at popcorn stage:

*Pedicle.*—Length 2 mm, diameter 2 mm.

*Pedicel color.*—Yellow Green 152C.

*Bud.*—Length 15 mm, width 12 mm.

*Bud color.*—Red Purple 69A.

Flowers at full bloom:

*Peduncle.*—Length 4 mm, width 1 mm, scaled, color Brown 200C to Black 202C.

*Corolla diameter.*—45 mm when fully open.

*Petals.*—Number: 5. Arrangement: separate. Color: Red Purple 69A fading to White 155D toward the center. Petal Veins: indistinct, color Red Purple 63B. Shape: broadly ovate. Margin: straight with occasional notching at the apex. Size: length 20 mm, width 15 mm. Texture: soft.

*Sepals.*—5 in number, wedge shaped, bluntly pointed, length 5 mm, width 3 mm, color Grayed Purple 185B on outer surface, Yellow Green 153 C with veination of Grayed Purple 185B.

*Filaments.*—Length 12 mm, width .1 mm, color White 155D.

*Anthers.*—Length 1 mm, width 0.5 mm, color Grayed Orange 167B, held slightly above filaments in a majority of blossoms.

*Ovary.*—Length 5 mm, width 4 mm, pubescent, color Yellow Green 145D.

*Stigma.*—Width 1 mm, pubescent, color Yellow Green 145D, held slightly lower than anthers in a majority of blossoms.

*Style.*—Length 4 mm, width 0.5 mm, color Yellow Green 145D.

Fruit:

*Maturity when described.*—Firm ripe.

*Date of picking.*—August 20, in Coloma, Berrien County, Mich., generally harvested in one picking, generally picked 2 to 3 days before Cresthaven (an unpatented selection).

*Size.*—Height 65 mm, width 75 mm, transverse diameter 83 mm.

*Fruit weight (firm ripe).*—210 g.

*Form.*—Oblate, even shoulders.

*Tip.*—Flat to slightly indented.

*Stem cavity.*—Width 18 mm, depth 3 mm.

Skin:

*Thickness.*—Medium thick.

*Texture.*—Smooth with very fine pubescence.

*Tendency to crack.*—Very slight.

*Color.*—80% to 90% blush of Red 39A with highlights of Red 53B with a background of Red 47A.

*Ground color.*—Yellow 13B.

Flesh:

*Aroma.*—High, sweet, aromatic.

*Color.*—Yellow Orange 19A with Red 46C around the pit and on an occasional outer edge, non-browning.

*Coloration at the pit.*—Red 46C bleeding to Red 44B in the flesh.

*Depth of coloration into the flesh.*—10 mm.

*Fibers.*—Very few, fine.

*Flavor.*—Excellent with high sweetness and medium acidity.

*Texture.*—Firm, somewhat rubbery, melting.

*Eating quality.*—Best.

Stone:

*Size.*—Length 35 mm, width 30 mm.

*Shape.*—Elongated, elliptical with a slight bulge on one side.

*Apex.*—Bluntly pointed, point does not extend from body of stone.

*Base.*—Flat, slightly tilted at abscission layer with stem.

*Surface.*—Deeply furrowed.

*Dorsal groove margin.*—Rough, slightly raised.

*Color.*—Grayed Purple 183A.

*Kernel.*—Elongated oval, length 20 mm, width 10 mm, color Yellow 18A, surface very slightly rough.

*Attachment to flesh.*—Freestone.

*Tendency to crack.*—Very low.

Use: Fresh.

Shipping quality: Excellent, can be graded on a commercial peach grader and shipped via truck.

Keeping quality: Excellent, will store for up to 2 months in common storage with minimal loss of flavor and color.

Tree winter hardiness: Average for a peach variety. Tree is hardy to 0° to −10° F.

Bud winter hardiness: 0° to −5° F., dependent on the stage of development of the bud.

Drought tolerance: Average for a peach variety. Normal requirements average ½ of rain per week. Severe drought adversely affects fruit size and quality.

Disease resistance: Moderately susceptible to Peach Canker (*Cytospora*), Bacterial Leaf Spot (*Xanthamonas*), Brown Rot (*Monilinia*) and other diseases. Susceptible to all know insect pests.

We claim:

1. A new and distinct variety of Peach tree, *Prunus persica*, substantially as herein shown and described.

* * * * *